(12) United States Patent
Suryanarayan et al.

(10) Patent No.: US 6,197,573 B1
(45) Date of Patent: Mar. 6, 2001

(54) SOLID STATE FERMENTATION

(75) Inventors: Shrikumar Suryanarayan; Kiran Mazumdar, both of Bangalore (IN)

(73) Assignee: Biocon India Limited (IN)

( * ) Notice: Subject to any disclaimer, the term of this patent is extended or adjusted under 35 U.S.C. 154(b) by 0 days.

(21) Appl. No.: 09/193,384

(22) Filed: Nov. 17, 1998

(51) Int. Cl.$^7$ .................................................. C12M 1/36
(52) U.S. Cl. .................................... 435/286.7; 435/291.3; 435/291.6; 435/294.1
(58) Field of Search ............................ 435/286.7, 289.1, 435/291.1, 291.3, 291.6, 293.2, 294.1

(56) References Cited

U.S. PATENT DOCUMENTS

| | | |
|---|---|---|
| 4,490,469 | 12/1984 | Kirby et al. . |
| 4,686,189 | 8/1987 | Redikultsev . |
| 4,767,705 | 8/1988 | Hang . |
| 5,595,910 * | 1/1997 | Kant et al. .......................... 435/289.1 |

FOREIGN PATENT DOCUMENTS

| | | |
|---|---|---|
| 2590903 | 6/1987 | (FR) . |
| 2166157 | 4/1986 | (GB) . |
| 61-128882 | 6/1986 | (JP) . |
| 09121843 | 5/1997 | (JP) . |
| 1406151 | 6/1988 | (SU) . |
| 1439120 | 11/1988 | (SU) . |
| 1463752 | 3/1989 | (SU) . |
| 1726397 | 4/1992 | (SU) . |
| WO 92/18623 | 10/1992 | (WO) . |
| WO 94/18306 | 8/1994 | (WO) . |

OTHER PUBLICATIONS

Ahmed, et al., "Design of Solid State Fermentor for Production of Fungal Metabolites on Large Scale" Biotechnol. Tech; 1(2),:97–102, 1987.

Adisasmito, et al., "Preparation of Fungal Starter Culture in Liquid Fluidized Bed Reactor", Biotechnol. Tech.; 1(3),: 75–180, 1987.

Almanza, et al., "Laboratory Scale Reactor for Aseptic Solid State Cultivation" Biotechnol. Tech; 9,6,:395–400, 1995.

Acuña–Argüelles, et al., "Production and Properties of Three Pectinolytic Activities Produced by *Aspergillus Niger* in Submerged and Solid–State Fermentation", Appl Microbiol Biotechnol 43:808–814, 1995.

Aidoo, et al., "Solid State Fermentations", Advances In Applied Microbiology, vol. 28 1982.

(List continued on next page.)

*Primary Examiner*—David A. Redding
(74) *Attorney, Agent, or Firm*—Choate, Hall & Stewart

(57) ABSTRACT

The present invention provides an improved solid state fermentation device that combines all of the operations of microorganism cultivation (sterilization, inoculation, cultivation, extraction, and post extraction treatment). This solid state fermentation device is modular in nature and operates in a contained manner so that the live microorganisms from the reactor cannot come into contact with the environment and pollute the environment and also so that the environment inside the bioreactor is aseptic. Another aspect of this invention allows fermentation of microorganisms without inhibiting the growth of the microorganism. Specifically, the bioreactor is designed to remove heat that accumulates inside the bioreactor during fermentation by conduction. Additionally, there is a mechanism to add fluid to the interior of the bioreactor that permits equal distribution and precise control of a variety of environmental parameters. For example, the bioreactor of the present invention provides a means to add nutritive media to the microorganisms at any time during the fermentation process without disturbing the fermenting microorganisms. Furthermore, the bioreactor of the present invention provides a mechanism to mix the contents of the bioreactor at any time and for any duration during the fermentation process. Finally, the present bioreactor provides a means of extracting desired microbial products from the bioreactor without opening the bioreactor.

70 Claims, 7 Drawing Sheets

OTHER PUBLICATIONS

Bahr, et al., "Solid–State Fermentation in Fluidized Fed Fermentors" Dechema–Biotechnol. Conf.; 5:587–590, 1992.

Castillo, et al., "Mixed Culture Solid Substrate Fermentation for Cellulolytic Enzyme Production", Biotechnology Letters, 16(9):967–972, Sep., 1994.

Chamielec, et al., "Pilot–Scale Reactor for Aseptic Solid–State Cultivation", Biotechnology Techniques, 8(4):245–248, Apr., 1994.

Das, et al., "Mass Balance and Thermodynamic Description of solid State Fermentation of Lignocellulosics by *Pleurotus Ostreatus* for Animal Feed Production" J. Ind. Microbiol; 15(1):25–31, 1995.

Deschamps, et al., "β–Gluosidase Production by *Aspergillus Phoenicis* in Solid State Fermentation", Biotechnology Letters 6(1):55–60, 1984.

Durand, et al., "A New Pilot Reactor for Solid–State Fermentation" Biotechnol. Bioeng.; 31(5):476–486, 1988.

Fung, et al., "Baffles Increase Performance of Solid–State Fermentation in Rotating Drum Bioreactors", Biotechnology Techniques, 9(4):295–298, Apr., 1995.

George, et al., "Production of Protease by *Bacillus Amyloliquefaciens* in Solid–State Fermentation" Process–Biochem; 30(5):457–462, 1995.

Gibbons, et al., "Intermediate–Scale, Semicontinuous Solid– Phase Fermentation Process For Production of Fuel Ethanol From Sweet Sorghum" Appl, Environ. Microbiol. 51(1):115–122, 1986.

Gumbira Sa'id, et al., "Operational Parameters for Packed Beds in Solid–State Cultivation", Biotech Adv. 11:599–610, 1993.

Han, et al., "Semisolid Fermentation of Ryegrass Straw", Applied Microbiology, 30 (5):930–934, Dec., 1975.

Hong, et al., "Optically Monitoring Baker's Yeast (Saccharomyces Cerevisiae) Growing in an Air–Fluidized/Expanded Potato Starch Matrix" J. Ind. Microbio; 2,(3),:187–193, 1987.

Johns, et al., "Production of Pigments by *Monascus Purpureus* in Solid Culture", Journal of Industrial Microbiology, 8:23–28, 1991.

Kargi, et al., "Solid–State Fermentation of Sweet Sorghum to Ethanol in a Rotary–Drum Fermentor", Biotechnology and Bioengineering, vol. 27 Aug., 1985.

Kerem, et al., "Effect of Manganese on Preferential Degradation of Lignin by *Pleurotus Ostreatus* During Solid–State Fermentation", Applied and Environmental Microbiology, 61(8): 3057–3062, Aug., 1995.

Larroche, et al., "Characterization of the Growth and Sporulation Behavior of *Penicillium Roquefortii* in Solid Substrate Fermentation by Material and Bioenergetic Balances", Biotechnology and Bioengineering, 39:815–827, 1992.

Larroche, et al., "Special Transformation Processes Using Fungal Spores and Immobilized Cells", Adv Biochem Eng. Biotech 55: 179, 1997.

Larroche, et al. "Spore Production of *Penicillium Roqueforti* in Fermentors Filled with Buckwheat Seeds: Batch and Semi–Continuous Cultivation", Appl Microbiol Biotechnol 24(2):134–139, 1986.

Lindenfelser, et al., "Solid–Substrate Fermentor for Ochratoxin A Production", Applied Microbiology, 29 (3):323–327, Mar., 1975.

Murthy, et al., "Biochemical Engineering Aspects of Solid–State Fermentation", Advances in Applied Microbiology, 38:99–147.

Ryoo, et al., "Evaporative Temperature and Moisture Control in a Rocking Reactor for Solid Substrate Fermenation" Biotechnol. Tech. 5(1):19–24, 1991.

Selvakumar, et al., "Purification and Characterization of Glucoamylase Produced by *Aspergillus Niger* in Solid State Fermentation", Letters in Applied Microbiology 23:403–406, 1996.

Steinkraus, et al., "Fermented Foods, Feeds, and Beverages", Biotech. Adv. 4:219–243, 1986.

Tanaka, et al., "Cultivation of Microorganisms in an Air–Solid Fluidized Bed Fermentor with Agitators", Biotechnology and Bioengineering, vol. XXVIII, 1294–1301, 1986.

Wiesche, et al., "Two–Step Degradation of Pyrene by White–Rot Fungi and Soil Microorganisms", 46 (5–6):653–9, Dec., 1996.

Vyas, et al., "Involvement of An Extracellular $H_2O_2$–Dependent Ligninolytic Activity of the White Rot Fungus *Pleurotus Ostreatus* in the Decolorization of Remazol Brilliant Blue R," Applied and Environmental Microbiology, 61(1):3919–3927, Nov., 1995.

* cited by examiner

FIG. 1
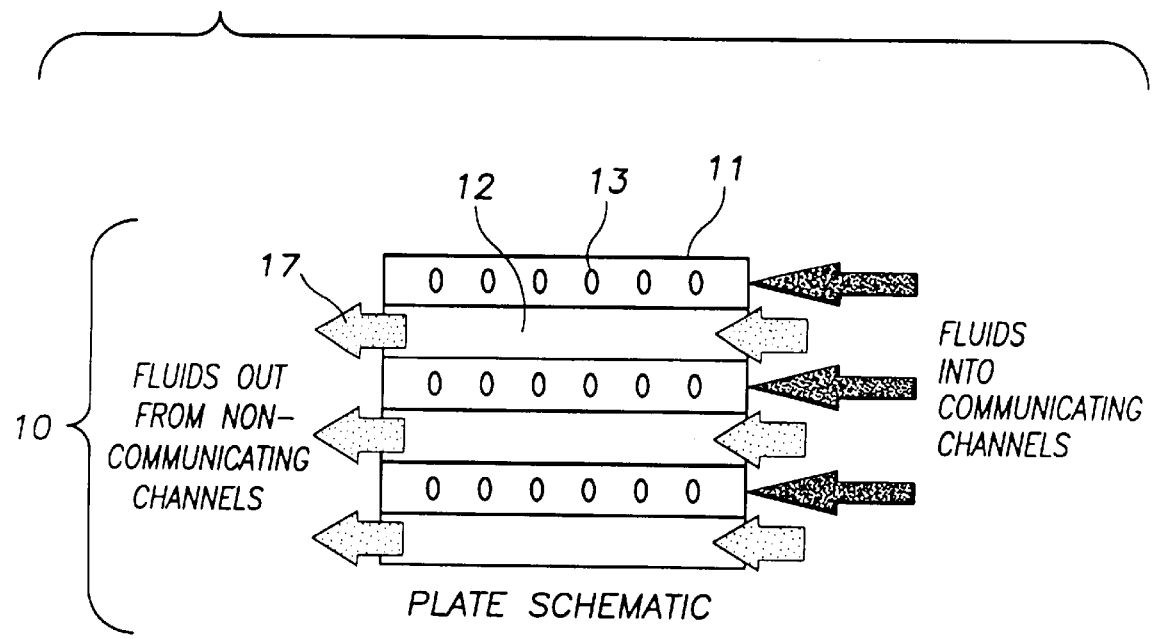
PLATE SCHEMATIC
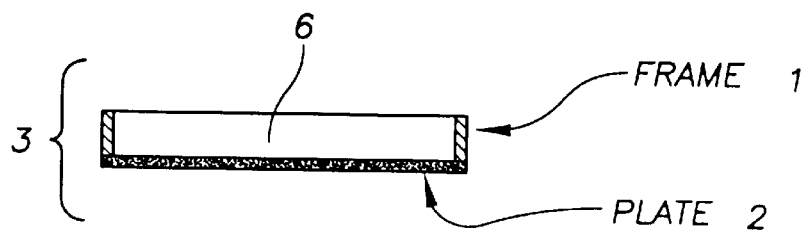
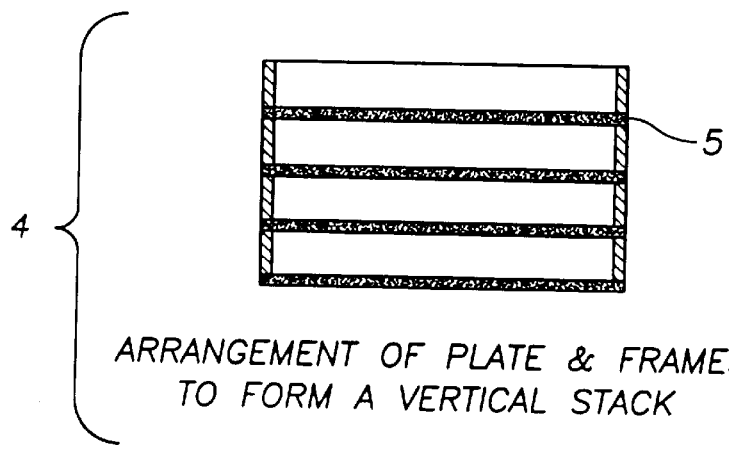
ARRANGEMENT OF PLATE & FRAMES TO FORM A VERTICAL STACK

PLAFRACTOR-MODES OF OPERATION

SOLID STATE FERMENTATION

BACKGROUND

Solid state fermentation has been practiced for centuries, most often in connection with food production, and can be defined as a technique for growing microorganisms, such as fungi, yeast and bacteria, on moist solid substrates. In recent years, there has been a resurgence of interest in solid state fermentation and its applicability to the production of enzymes, metabolites and organic compounds. Solid state fermentation devices provide several advantages over the commonly used process of submerged fermentation in product yield, cost and ease of use. Despite their economic advantages, the commercialization of solid state fermentation devices for industrial use has been limited for lack of efficient and practical designs.

A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37–52; Smits et al., "Solid-State Fermentation-A Mini Review, 1998), Agro-Food-Industry Hi-Tech, March/April, pp. 29–36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra).

A major problem in both static and agitated solid state fermentation systems is obtaining efficient removal of heat that is generated during the fermentation process. One method of heat removal employed by numerous solid state fermentation systems is aeration. The disadvantage of using aeration as the means of heat removal is that not only is heat removed, but water is also evaporated from the solid matrix, leading to desiccation of the substrate. Constant aeration also makes it more difficult to maintain a stable environment inside the bioreactor with respect to oxygen and carbon dioxide concentrations. Another means of avoiding heat build up is mixing the substrate bed. Unfortunately, mixing during fermentation leads to damage of the cells and gross aggregation of substrate particles. Aggregation of substrate leads to inhomogeneities in local substrate temperature resulting in local differences in biomass growth and activity. These problems are compounded in the large scale systems often required for industrial preparation of certain products. The large scale practice of solid state fermentation using the devices available in the art has the additional disadvantage of being labor intensive.

The steps involved in solid state fermentation include, 1) sterilization of the cultivation device and the cultivation media, 2) inoculation of the cultivation media with the microorganisms, 3) cultivation of the microorganisms 4) extraction of biological products from the cultivated microorganisms, and 5) post extraction treatment of the waste materials and the cultivation device. It is also desirable that the cultivation system provide a mechanism whereby the growth environment during the cultivation process is precisely controlled such that specified conditions are maintained throughout the cultivation process. None of the devices available for solid state fermentation to date provide for carrying out all of the steps required for solid state fermentation in a single fermentation device. Up to now, the practice of solid state fermentation has involved carrying out multiple manipulations which are both tedious and impractical. Such manipulations often risk exposing the cultivation environment to contaminants from outside the cultivation environment, preclude the ability to efficiently and precisely control the cultivation, and lead to reduced product quality and/or yield.

There exists a need for a compact reactor that combines all the operations involved in solid state fermentation into a single device capable of operating in a contained manner and controlling the environment within the bioreactor without inhibiting growth of the microorganism. Furthermore, there exists the need for a device that will allow homogeneous addition of chemicals and nutrients to a bioreactor without contamination.

SUMMARY OF THE INVENTION

The present invention provides an improved solid state fermentation device for the cultivation of microorganisms. In general, the invention provides a bioreactor and a process for using the bioreactor for the cultivation of microorganisms on solid media. The Applicants herein refer to the bioreactor of the present invention as a PLAFRACTOR™. In preferred embodiments, the invention provides a bioreactor that is modular in nature and carries out all of the processes of solid state fermentation in a single, contained environment. The modular nature of the bioreactor allows the size of the bioreactor to be adjusted to suit the user's need. The construction of the bioreactor allows solid state fermentation to be carried out in a manner such that the fermenting microorganisms are kept isolated from the outside environment during the course of the fermentation process. In certain preferred embodiments, the environment inside the modules is precisely controlled to meet specified conditions.

One aspect of the bioreactor is a mechanism to remove heat that accumulates inside the bioreactor during fermentation by conduction. Specifically, the bioreactor is constructed by stacking individual modules. The modular construction of the bioreactor provides multiple modules stacked on top of one another, each with a base connected to a frame for holding the solid medium in isolation from the exterior environment. The base plate of the bioreactor has multiple channels, called non-communicating channels, that carry heating and cooling fluids sandwiched between two sheets. Heat is transferred to and from the modules by conduction. In this way the temperature of the module is precisely maintained to meet the specific requirements of different microorganisms.

Another aspect of the bioreactor is a mechanism to add fluids to the interior of the modules. In this embodiment, the base of the module mentioned above contains a second set of channels, called communicating channels, to deliver fluids to the inside of the module thereby providing a way to adjust the moisture and oxygen content within the bioreactor. For example, for optimum growth, some microorganisms require high carbon dioxide concentrations. Another aspect of this embodiment provides a mechanism by which compounds of interest can be extracted from the microorganisms. For example, extracting fluids can be sent through the communicating channels for extracting the compound of interest for collection. In yet another aspect of this embodiment, the communicating channels can send steam, gas (e.g., ethylene oxide or ozone), or chemicals (e.g., beta-propiolactone, hydrogen peroxide or pyrocarbonic acid diethyl ester) into the bioreactor for sterilization of the bioreactor and its contents before and after fermentation. A final aspect of the present invention is that materials, (e.g., chemicals and/or nutrients), can be added to the bioreactor while the bioreactor is in operation.

In a further embodiment, the present invention provides a mechanism to mix the contents of the bioreactor. According to the present invention the interior of each module has a mixing arm that revolves about the central axis of the module while rotating. Mixing can be carried out at any point in the fermentation process that mixing is deemed to be appropriate. Preferably, mixing occurs after inoculation of the media inside the bioreactor to evenly distribute the inoculum into the media within the bioreactor.

The teachings of the present invention are particularly applicable to the production and extraction of microbial products. In certain preferred embodiments, the microorganisms produce a biologically useful product that can be extracted from the microorganism in the bioreactor and harvested for medicinal and industrial uses. Some examples of medicinals that can be produced by the present invention are lovastatin and cyclosporin. Product that can be used in industrial applications include the microbial enzyme rennet and peptidase. Any of a variety of microbial organisms may be employed according to the present invention.

DESCRIPTION OF DRAWINGS

FIG. 1 is a schematic of a circular bioreactor.

DETAILED DESCRIPTION OF PREFERRED EMBODIMENTS

Definitions

Figure 2:
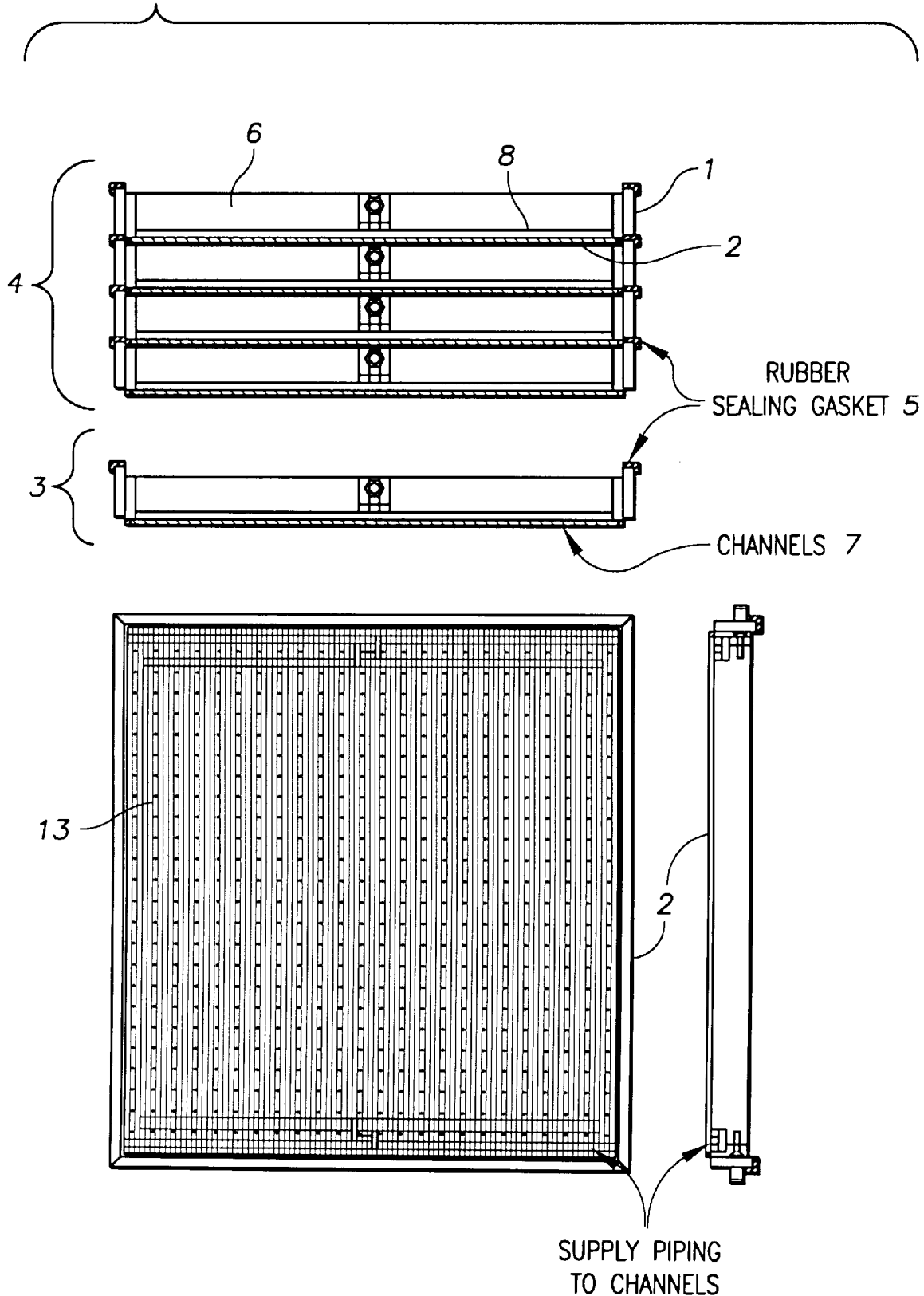
FIG. 2 is a schematic of a rectangular bioreactor.
Figure 3:
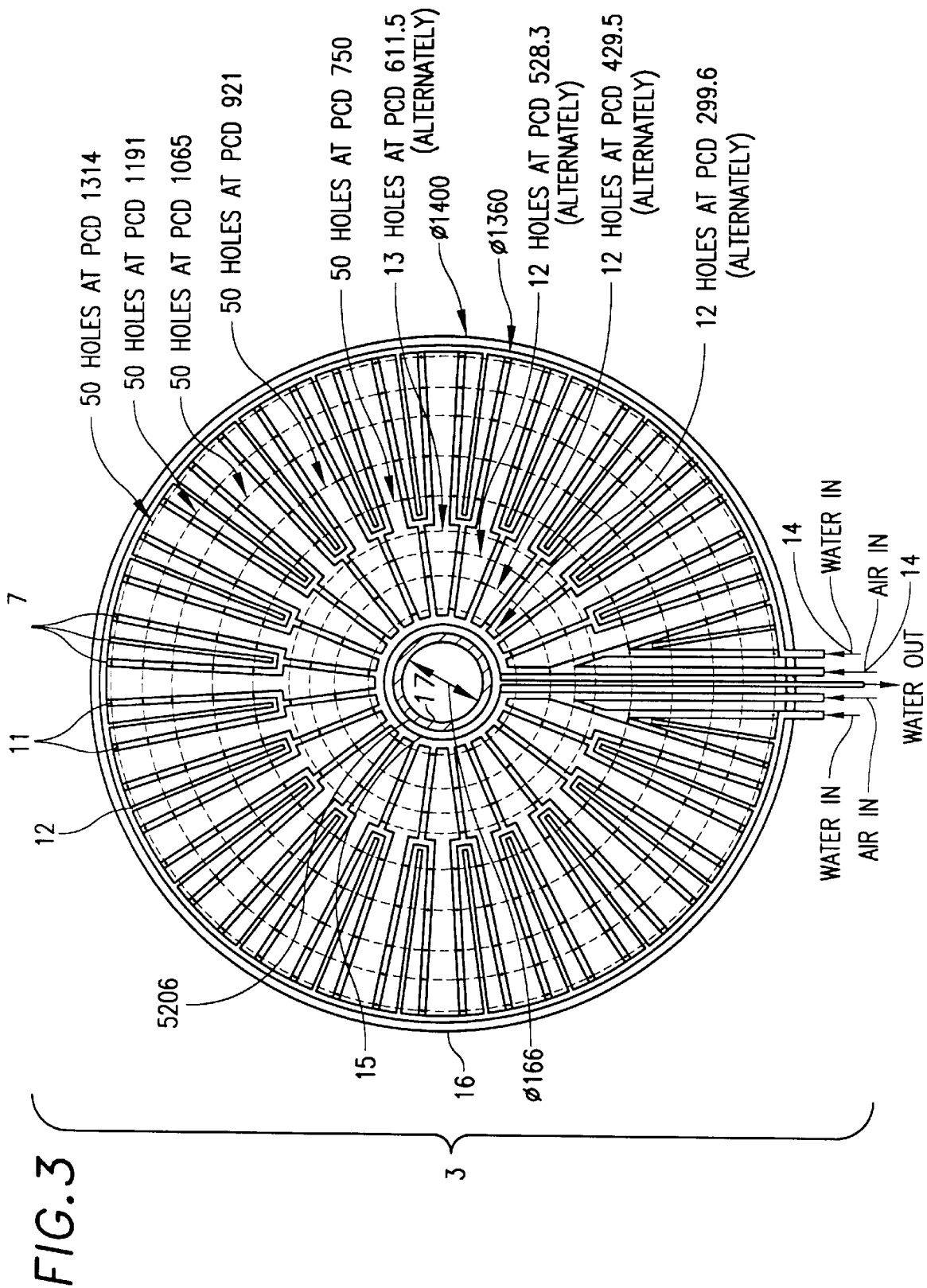
FIG. 3 is a schematic representation of the communicating and non-communicating channels in a base plate and the arrangement of the base plate and frames to form a vertical stack.

"Solid state fermentation" or "solid state cultivation": The term "solid state fermentation" or "solid state cultivation", sometimes referred to as "semi-solid state fermentation" as used herein, means the process of fermenting microorganisms on a solid medium that provides anchorage points for the microorganisms in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable.

"Bioreactor": The term "bioreactor" as used herein, means a device capable of holding fermentation media inoculated with microorganism and carrying out the process of solid state fermentation in a contained manner. A bioreactor can be used to grow any microorganism capable of growing under specified conditions in a contained environment. Some examples of microorganisms capable of growing in a bioreactor are fungi, yeast and bacteria. Particularly preferred microorganisms are fungi. Fugi that can be used in the present invention include septate and aseptate fungi. Septate fungi can be either extracellular or intracellular septate fungi.

"Cultivation plant": The term cultivation plant as used herein refers to the bioreactor capable of growing microorganisms in a contained environment plus the auxiliary machinery required to operate the bioreactor device. A cultivation plant, according to the present invention consists of several connected stacks of modules in combination with auxiliary equipment associated with operating the cultivation plant. Some examples of auxiliary equipment are temperature probes, humidity sensors, exhaust gas analyzers, pressure sensors, air flow sensors, seed fermentors, water or nutrient addition tanks, control pipe racks and weight sensors. Various other utilities that can be automated by computer include movement of cooling water, steam, and filtered condensed air. Others include the operation of the vacuum, seed transfer, water or nutrient addition to the modules and control of the pipe rack. Such examples of auxiliary equipment and computer automation are well known in the art.

"Modules": Module, as used herein, refers to a structure formed by a base plate and a frame. The base plate forms the bottom and the frame forms the sides of a structure that can serve as a container for holding media. Individual modules also have other components that allow the control of the environment of the module for example, mixing arms, and communicating and non-communicating channels which are described in detail below. Individual modules may be stacked on top of one another to form a sealed interior environment that prevents leakage of the contents of the modules into the outside environment, and also prevents contamination of the interior of the module with particles from environment outside the module.

"Stack": As used herein the term "stack" refers to the plurality of modules within a cultivation plant that are placed on top of one another to create a bioreactor of adjustable height.

"Contained": The term "contained" as used herein covers both the definitions for "contained" and "aseptic". The word "contained" implies that the bioreactor is capable of containing the microorganisms that are growing within the bioreactor (e.g. live microorganisms from the reactor cannot come into contact with the environment and pollute the environment). This feature is particularly useful if the bioreactor is used to cultivate pathogenic microorganisms or genetically modified microorganisms that local regulations often require to be grown in contained equipment. The definition of "containment" focuses on saving the environment from the reactor contents, not saving the reactor contents from the environment. For example, it is possible to achieve containment by having a low pressure system that only brings things into the bioreactor from the outside environment, but does not allow the contents of the bioreactor to contaminate the outside environment.

The "aseptic" manner in which the bioreactor of the present invention operates such that it protects the contents of the bioreactor from contamination by the environment. Aseptic operations are useful because only the desired microorganisms are allowed to grow inside the bioreactor, producing a homogeneous desired product, reproducibly. The aseptic environment ensures that the final products are not contaminated with an unknown external microorganism that would bring variability to the production process.

Thus, the bioreactor operates in a contained manner, ie., the bioreactor protects the contents of the bioreactor from contamination by the environment and protects the environment from its contents. Another advantageous aspect of the bioreactor operating under a contained environment is that the moisture content, oxygen content, and temperature can be precisely controlled to meet desired conditions.

"Naturally produced": The term "naturally produced", as used herein, means a protein or chemical product that is produced by a microorganism in its natural environment without human intervention or genetic manipulation.

"Genetically altered": The term "genetically altered" or "genetically modified" is used herein in reference to any biological product produced by a microorganism as a result of human intervention by genetic manipulation or the microorganism itself that has been altered by genetic engineering or recombinant DNA technology. For example, a gene encoding a particular protein of interest can be introduced into a microorganism by recombinant DNA technology so that the microorganism produces that protein (See Ausubel et al., "*Current Protocols in Molecular Biology*", Greene Publishing Associates, New York, V. 1&2 1996, incorporated by reference herein).

"Fluid": The term "fluid" as used herein means any substance that can be passed through a communicating or non-communicating channel. Some non-limiting examples of fluids are water, steam, and sterile air. The fluid may be any nutritive media containing microorganisms.

"Channels": "Channels" as used herein, means any passageway capable of conducting a substance, for example air or water. Channels is used herein includes both communicating and non-communicating channels. Channels can be differentiated from tubes (or pipes) in that tubes are a particular type of construction that form passageways for the passage of fluids. For example, one base plate construction involves welding tubes together. The tubes serve as the communicating and non-communicating channels.

Solid State Fermentation

As mentioned above, the present invention provides a bioreactor for cultivating microorganisms on solid medium under specified conditions. The bioreactor is constructed such that it combines all the operations involved in carrying out solid state fermentation into one device, the operations comprising (a) sterilizing the cultivation device and the cultivation media placed inside the device;

(b) inoculating the cultivation media with the microorganisms;

(c) cultivating the microorganisms under specified conditions;

(d) extracting biological products from the cultivated microorganism; and (e) post extraction treatment of the waste materials and the cultivation device.

The device of the present invention provides significant advantages over known and existing methods for cultivating microorganisms on solid media in the areas of containment, material handling, control of the cultivation process, addition of chemical nutrients during the process, extraction of products of interest and treatment of residues prior to waste disposal. Containment, as used herein, refers to both the contained and aseptic nature of the bioreactor. For example, the bioreactor operates in a contained manner by protecting the contents of the bioreactor from contamination by the outside environment (operating in an aseptic manner) and by protecting the environment from the potentially harmful or pathogenic microorganisms growing within the bioreactor (operating in a contained manner). The contained nature of this device allows the entire process of solid state fermentation to be carried out in isolation from the outside environment, in addition providing the advantage of maintaining a sterile environment throughout the entire fermentation process. The contained nature of the bioreactor according to the present invention further provides the ability to sterilize, inoculate and control the fermenting medium temperature and moisture content in situ. Furthermore, the extraction of a biological product from the fermenting medium can be achieved without having to dismantle or open the reactor. Following extraction of the product, the reactor contents may be sterilized in situ. The reactor may then be dismantled to discard the sterilized, spent substrate, cleaned and reused for the next fermentation cycle.

The reactor achieves containment in the following ways:

1) The bioreactor contents are sterilized prior to inoculation eliminating all microorganisms from within the bioreactor prior to the start of the fermentation process.

2) The transfer of inoculum from the seed vessels to the bioreactor can be achieved without exposing the microorganism to the environment (e.g., through sealed, sterilized tubes connected between the seed vessel and the reactor with the transfer taking place through a pressure differential between the seed vessel and the bioreactor). This method also protects the microorganism being transferred from contamination by the environment.

3) Air that is vented out from the reactor (which might carry spores of the microorganism being cultivated) is vented through an exhaust gas filter which is capable of trapping microorganisms. Such exhaust gas filters are well known in the art and are used as standard equipment for submerged fermentations). Air that is sent into the bioreactor can also be filtered similarly to prevent contamination of the reactor contents.

4) After the product has been extracted from the bioreactor, the reactor may be sterilized in situ. Any live microorganisms in the reactor are destroyed before the device is opened and its contents are allowed to come into contact with the environment.

The Bioreactor

The bioreactor of the present invention (refer to FIGS. 1–5) is constructed of multiple individual modules 3 that can be fitted on top of one another to form a "stack" 4 of any convenient height. The stacked modules operate in parallel to create a single functional unit, referred to herein as a "cultivation plant", or "bioreactor". The bioreactor may be constructed of any suitable material that permits operation, two examples being, but not limited to stainless steel and polycarbonate. Each individual module has a plate 2 that forms the bottom of the module and a frame 1 that forms the sides of the module. In certain preferred embodiments the shape of the module is square. For example, a square frame fitted on top of a square base. In another preferred embodiment the shape of the module is rectangular. In other preferred embodiments the shape of the module is circular. Preferably the shape of the module is circular.

The plate 2 forms the base of the module and will be referred to herein as the "base plate". The frame 1 is mounted on top of the base plate and sealed in such a manner that prevents leakage from within the modules to the outside environment. One non-limiting example of a seal is a rubber gasket 5 that fits between the bottom of the base plate 2 of one module and the rim of the frame 1 of another module and is tightened by compression or downward pressure to ensure the seal is secure. The frame 1 forms the sides of the module and functions to form a container to retain the media. Preferably, the height of the frame is 4–8 centimeters. In one preferred embodiment the media placed inside the bioreactor 6 is solid media. Microorganisms capable of growing on solid media may be cultivated according to the present invention. The dimensions of the modules and the size of the stack of modules can vary to be as large as is convenient to the circumstances in which it is to be used.

The base plate may be one of two basic constructions. In one embodiment, the base plate is constructed of tubes 7 sandwiched between two flat sheets made of any material capable of conducting heat 8. The tubes are spaced apart from one another to allow a channel to form between the adjacent tubes. The sides of the channel are formed by the tubes and the top and bottom of the channel are formed by the flat sheets. These channels are the non-communicating channels as will be discussed in greater detail below. In yet another embodiment, the base plate is constructed by laying multiple tubes beside each other on a flat plane and welding them together. In this particular embodiment, the tubes need not be sandwiched between the sheet.

As mentioned above, the modules may be of any convenient size or shape. In a square or rectangular construction, the channels 7 run parallel to each other. For example, laying multiple tubes beside each other on a flat plane and welding them together 10. In a circular construction (see FIG. 3), a set of tubes 7 radiate out in a circular pattern from the central axis of the module.

It is an important aspect of the present invention that two separate sets of channels are formed, these being the communicating 11 and non-communicating 12 channels. The communicating and non-communicating channels alternate with each other in their arrangement in the base plate 2. The communicating channels carry fluids into the module so that the fluids contact the interior of the module. The communicating channels, in the circular construction, also branch out in the form of a "Y" as they radiate out, to ensure an equal distribution of the fluids coming through the tubes to the inside of the module. Holes 13 drilled into the communicating channels 11 allow the fluids to exit the communicating channel 11 and contact, for example, the solid matrix that is contained within the module 6. The holes 13 are arranged in such a way that each hole 13 services an equal surface area of the plate 2. Holes 13 are also drilled into the metal sheets 8 sandwiching the communicating 11 channels that line up with the holes 13 in the communicating channels 11 such that fluids carried by the communicating channels 11 can be distributed to modules 3. In a module of square construction the holes are preferably spaced with equal distance between them. In a module of circular construction 3, the spacing between the holes preferably reduce progressively from the center to periphery, to compensate for the non-linear increase in the area of the plate with increasing radius.

Those of ordinary skill in the art will appreciate that any of a variety of fluids can be distributed by the communicating channels 11. In one preferred embodiment, the interior bioreactor 6 can be sterilized by sending steam through the communicating 11 and non-communicating 12 channels. In another preferred embodiment, the communicating channels 11 may be attached to a vacuum source prior to sterilization to remove air from inside the bioreactor. The sterilization process may be carried out either using steam or a sterilizing gas, for example ethylene oxide. Adequate conditions for sterilization, using either steam or gas, may be determined easily by those skilled in the art. In other preferred embodiments, the culture media is inoculated with microorganisms by sending fluid containing microorganisms through the communicating channels 11. The fluid containing the microorganisms may be a nutritive media.

Once the microorganisms are growing inside the bioreactor another aspect of the invention provides that the environment within the bioreactor can be adjusted using the communicating channels 11. For example, the humidity of the module can be adjusted by sending water into the module through the communicating channels 11. Additionally, chemicals and/or nutrients may be added through the communicating channels while the operation of the bioreactor is in progress (a process referred to in the art as "fed batch"). Addition of the chemicals and/or nutrients is carried out so that distribution of the chemicals and/or nutrients is homogeneous (e.g., even distribution throughout the bioreactor). For example, it is advantageous to add sugar to the fermentation medium once the fermentation is underway. The ability to continuously feed the microorganisms instead of giving them a limited starting amount of nutrients that steadily declines throughout the fermentation process (e.g., as with solid surface fermentation) results in a higher quality product and greater product yield. It can also be inhibitory for microbe growth to add a bolus of nutrients at the start of the fermentation process. It is preferred that the nutrients are restricted to non-inhibitory levels for optimal growth of the microorganism.

The communicating channels 11 alternatively can be used to adjust the oxygen content within the module by sending through the communicating channels 11 sterile air. Likewise, the carbon dioxide or nitrogen content of the module may be adjusted to specified conditions, the range of which is significantly improved over that of submerged fermentation. Indeed any gas may be added to the bioreactor at precisely controlled levels. Thus, the apparatus of the present invention offers significant advantages, previously unavailable in the art.

Once the microorganisms have completed the growth phase it may be desirable to send extracting liquids, such as organic solvents, through the communicating channels 11 in order to separate out the biological compound of interest. By way of further demonstration, upon completion of the extraction process, the waste materials can be appropriately treated while still contained within the bioreactor by sterilization and any other means appropriate for the waste generated. These examples are understood to demonstrate the multiplicity of fluids that can be applied to the interior of the bioreactor by way of the communicating channels 11 and are not meant to limit the scope of the utility of the communicating channels 11.

It is another aspect of the construction of the present invention that the communicating channels 11 be connected to a distribution port 14 that delivers fluids to the communicating channels 11. The location of the distribution ring 15 can vary depending on the shape of the module 3. In the square construction (FIG. 1, 2, and 4) of the present invention, the distribution port 14 is located at one end of the module. In the circular construction of the present invention, a distribution "ring" 15 is centrally located with the communicating channels 11 radiating outward from the central distribution ring 15.

The bioreactor is further assembled such that alternate plates of the stack are designated emitter 23 and collector 24 plates respectively (See FIG. 5). Emitter plates 23 allow fluids into the bioreactor and collector plates 24 allow passage of fluids from the bioreactor. There are valves on the pipes that bring in the fluids to these plates. The pipes and valves are on the communicating channels, which carry fluids that come into contact with the medium inside the reactor. In preferred embodiments, sterilization, inoculation and fermentation, steam inoculum are sent in and vented either through the emitter 23 or collector 24 plates respectively. The direction of flow can be reversed as required by the process. One instance that might require reversal of the direction of flow is if a moisture gradient has built up in the bioreactor. The direction of air flow can be reversed to move the accumulated moisture in the other direction.

During the sterilization and fermentation operations, other preferred embodiments provide a means of building up a back pressure by partly closing the vent valves. In a final embodiment, during extraction, the extracting fluids are sent in from the top emitter plate 23 and the extracted material is removed from the bottom collector plate 24. During this process, the valves connected to the intermediated plates are kept closed. Only the valves to the top and bottom plate remain open. It is also possible to extract by sending in extracting fluids from a bottom emitter plate 23 and collecting it from a top collector plate 24.

A particular feature of the construction of the bioreactor that makes this extraction process possible, is that the communicating channels of the intermediate plates, positioned between the top and bottom plates, have holes that go all the way through the tubes for distribution of fluids to the modules above and below the plate. The top plate has holes drilled only into the bottom of the tubes forming the communicating channel and the bottom plate has holes drilled only into the top of the tubes forming the communicating channels. This feature allows the extracting, or other fluids, to be added, for example, to the top plate, from where the fluids trickle down through each intervening plate to the bottom plate. The extracted substance may then be collected from the bottom plate. Of course, the through holes do not have to be limited to the intermediate plates. Additionally, the arrangement of the through holes on the tube can differ from that described above, for example, the holes may be staggered instead of across from one another.

As is well known in the art, concave dished ends 21 can be placed under the bottom plate and over the top plate (see, FIG. 4) to collect the extract which comes from through holes in the communicating channels of the top and bottom plate. These dished ends, while not absolutely necessary for the operation of the bioreactor, provide extra safety while operating the reactor under high pressure. Dished ends are standard for vessels that operate under pressure as they are capable of withstanding pressure better than flat ends.

As stated above, the tubes form communicating 11 and non-communicating 12 channels. The non-communicating channels 12 alternate with the communicating channels 11 in arrangement and unlike the communicating channels 11, do not have holes 13 drilled therein. The non-communicating channels 12 carry heating and cooling fluids through the base plate 2 and function to control the temperature of the environment within the module 3 by conduction. One example of a fluid that can be used to heat or cool the module 3 is water. Alternatively, any fluid that can heat or cool the module 3 by conduction may be used in the present invention. Preferably the temperature within the module 3 is monitored and adjusted to meet specified conditions according to the operation being preformed. In one embodiment of the present invention, the bioreactor has inserted into it a probe capable of monitoring the temperature of the modules. According to the present invention, the temperature inside the module 3 can be adjusted to a range of temperatures. For example, when sterilizing the bioreactor, one would want to heat the modules 3 to a very high temperature. In another example, when growing microorganisms one would want to maintain a temperature appropriate for growing that specific microorganism.

The non-communicating channels 12 of the present invention are joined to a system of headers 16 that are located around the periphery of the module 3 and also may be sandwiched between the two metal sheets 8. This header arrangement 16 delivers fluids to the non-communicating channels 12. As mentioned above, the modules 3 can be a variety of shapes, therefore the header 16 arrangement can also vary in shape to fit the module 3 to which it is applied. If the module 3 is square, the header arrangement 16 may be located on the side of the module 3. If the module 3 is circular, the header arrangement 16 must be of the appropriate diameter and construction to deliver fluids to the non-communicating channels 12 radiating from the outside inward toward the center of the module 3. This variability in size and construction also applies to the collection port 17. On a square module 3 (see, FIG. 1) the collection port 17 may be located on the side to the module 3. If the module 3 (see, FIG. 3) is circular, fluidsleave the base plate through a "collection ring" 17 that is concentric with the distribution ring 15 described above and just inside of the distribution ring 15. The diameter of the inner collection ring 17 is chosen to be larger than the diameter of the distribution ring 15, thereby fluids coming into the non-communicating channels 12 from the circular header at the periphery can slip over the distribution ring 15 and flow into and out through the collection ring 17. One of ordinary skill in the art will understand that the constructions described above are only set forth by way of example and that the header arrangement 16 and the collection port 17 can be constructed in any way that ensures that their functions are maintained.

Figure 4:
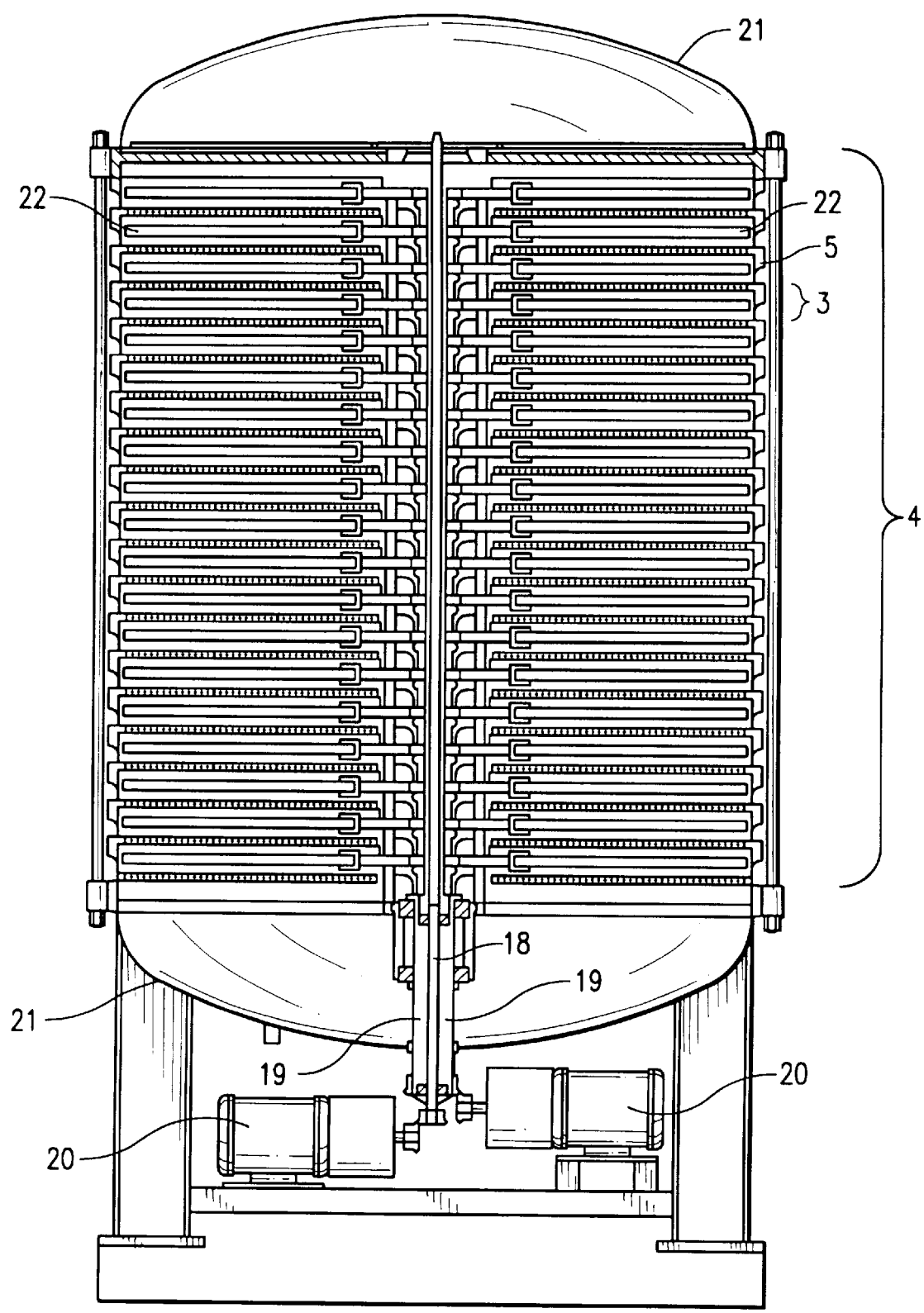
FIG. 4 is a schematic of a stack of modules sealed with rubber gaskets and an overhead view of the communicating and non-communicating channels in a single module.
Figure 5A:
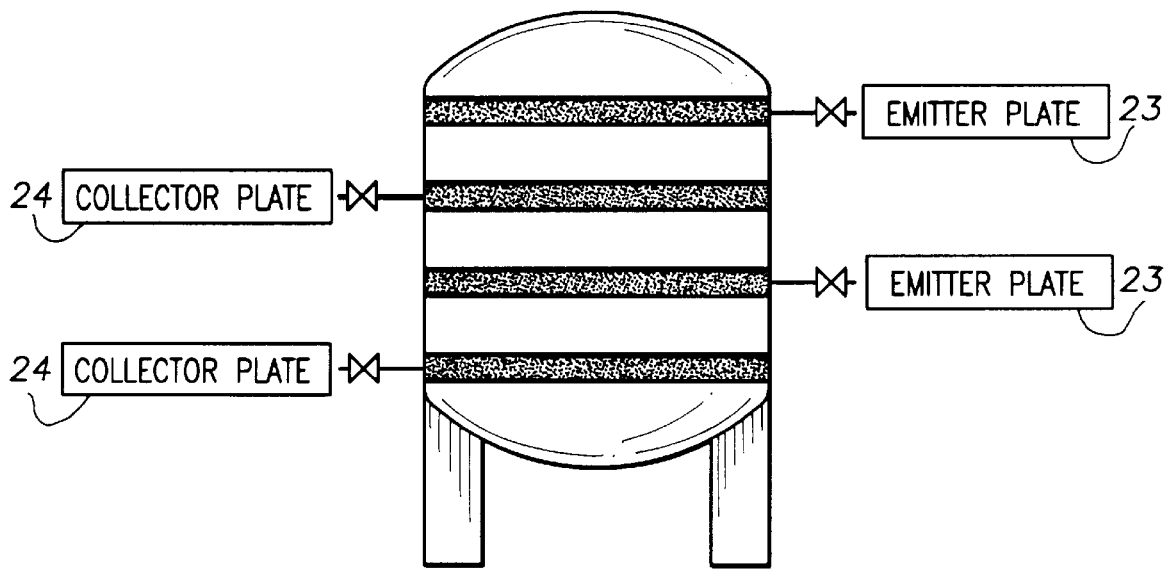
FIG. 5 is a schematic depicting the emitter and collector plates (top) and flow of fluids through the bioreactor during sterilization (middle) and extraction (bottom).
Figure 5B:
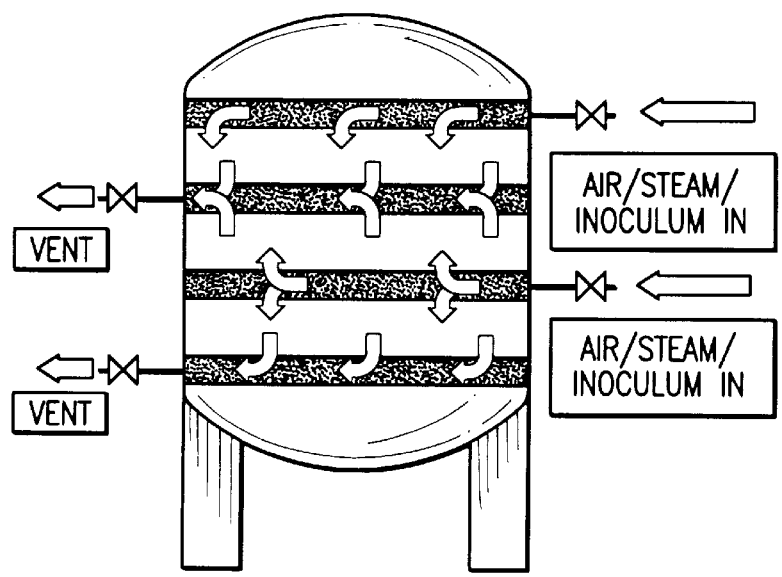
Figure 5C:
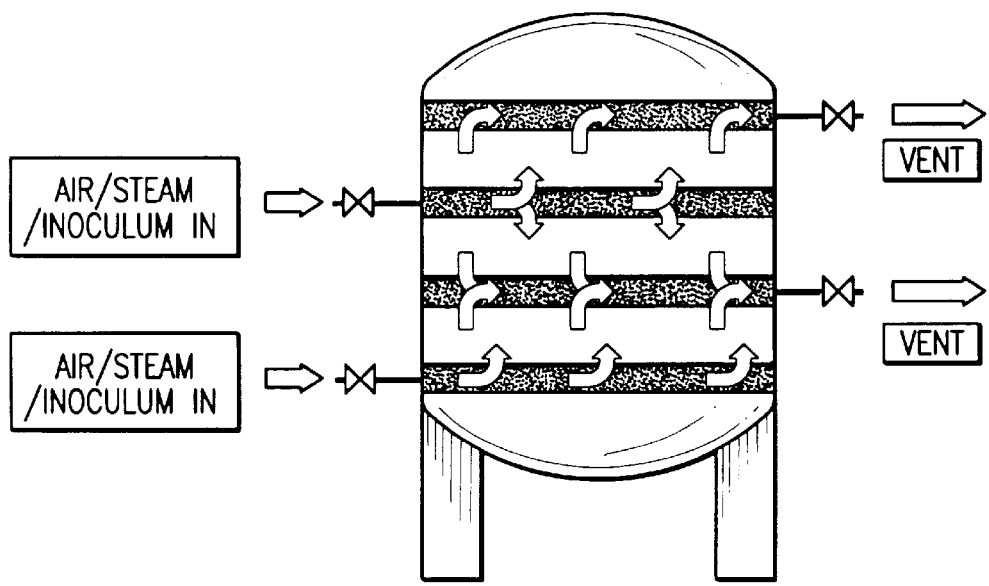
Figure 5D:
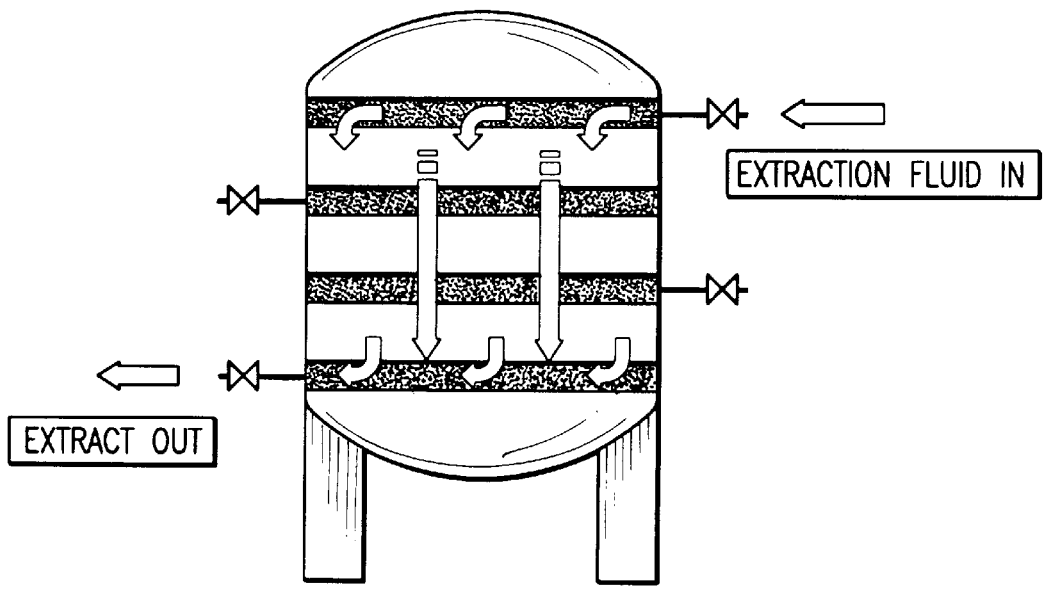

In addition to a base plate 2 and frame 1, each module may also have a mixing arrangement (FIG. 4 18). The function of the mixing arrangement 18 is to agitate the solid media inside the module 6. Agitation may be carried out, for example, after the media has been inoculated with the microorganism. Agitation may also be carried out during the process of extracting biologically useful products from the microorganisms. One of skill in the art will realize that agitation can be carried out at any time during the fermentation process that agitation is deemed to be necessary, although, preferably, excessive mixing does not occur during the fermentation process due to the potential of damaging the microorganisms, specifically fungi.

Figure 6:
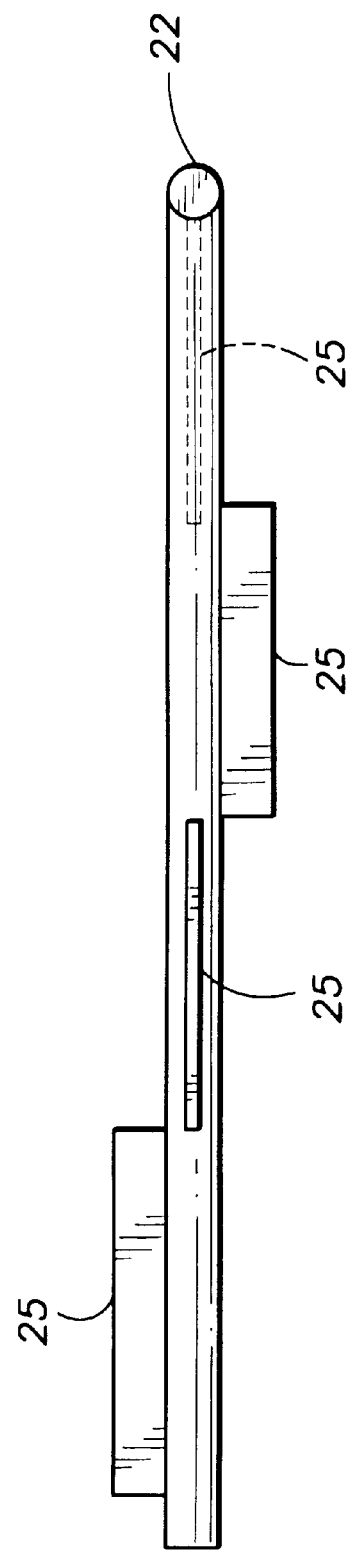
FIG. 6 is a diagram of a mixing arm with blades.

In the present invention, the mixing arrangement 18 is preferably placed at the center of the module 3. In one aspect of the invention the mixing arrangement has one or more mixing arms 22, preferably two mixing arms. The mixing arms may be equipped with, for example flat blades 25 (see FIG. 6), but can also be equipped with teeth, or any other modification that would assist in the mixing process required for the particular application the bioreactor is being used. A particularly preferred blade construction is one in which short blades are staggered about the diameter of the mixing arm, but no side by side gap or horizontal overlap exists between the short blades.

In another aspect of the present invention, the mixing arms rotate as they revolve around the central axis of the module. This rotation while revolving may be achieved by two concentric shafts 19 at the center of the mixing arrangement and driven by two independent motors 20. The inner shaft may rotate the two mixing arms, while the outer shaft revolves the arms around the central axis of the module. The particular arrangement of shafts and motors described here is not meant limit the invention to this one arrangement. Any placement of the mixing arrangement that accomplishes simultaneous revolution and revolving can be considered within the scope of the claimed invention. For example, the present invention can use a motor with a planetary gear system.

A particularly preferred aspect of the mixing aspect of the present invention is that the speed of the revaluation of the revolving arm about the central axis be adjusted to a precise ratio with respect to the speed of rotation of the arm. This aspect is critical to the proper mixing of the contents of the bioreactor in order to prevent movement of the contents of the bioreactor in a bulk fashion. To prevent the contents of the bioreactor from being pushed in a circular motion in a mass, the mixing arm revolves only a distance equal to that which can be cleared by the rotating blades which lift the media that is in front of the rotating arm and deposit it behind the rotating arm. If two separate motors are used to control the mixing arrangement, the speed of each motor can be controlled separately. If one motor is used, the ratio of revolution to rotation can be precisely adjusted by gear selection so that these movements are orchestrated to achieve efficient mixing and equal redistribution of the contents of the bioreactor.

As previously mentioned, the bioreactor is constructed in such a way to allow precise control of the environment inside the bioreactor 6. In order to accomplish this, it may be desirable to equip the bioreactor with probes capable of monitoring the environment inside the bioreactor. Probes may be required to monitor temperature, humidity, oxygen concentration or carbon dioxide concentration inside the bioreactor 6. Other probes include exhaust gas analyzers, pressure sensors, air flow sensors and weight sensors. Furthermore, certain operations of the bioreactor are amenable to automation, (e.g., movement of cooling water, steam, filtered condensed air, operation of the vacuum, seed transfer, water or nutrient addition and control of the pipe rack, and turning on and off motors and pumps at specific times). Such auxiliary equipment as listed above are commonly used for automation of submerged fermentation and would be known to any person skilled in the art.

Operation of the Bioreactor

The bioreactor of the present invention, as stated above, permits one to carry out all of the steps of solid state fermentation in a single device and in a contained manner. The bioreactor of the present invention carries out the steps of 1) sterilization of the cultivation device and the cultivation media, 2) inoculation of the cultivation media with the microorganisms, 3) cultivation of the microorganisms 4) extraction of biological products from the cultivated microorganisms, and 5) post extraction processing, without exposing the materials inside the modules of the bioreactor to the outside environment. The bioreactor of the present invention also regulates precisely, the growth environment inside the bioreactor. These aspects of the present invention provide an enormous convenience over previous solid state fermentations devices that require multiple manipulations at each step in the fermentation process, for example autoclaving the media outside of the solid state fermentation device and then transferring the media to the fermentation device.

According to the present invention, the process for using the bioreactor for the cultivation of microorganisms first involves filling the cleaned modules 3 with the fermentation medium 6. Any solid state fermentation medium may be utilized in the present invention. Some examples of solid state mediums are maize bran, corn, wheat soya hull, soya beans, other cereals, minerals (e.g., vermiculite, celite, polyurethane foam), or any support material capable of absorbing aqueous solutions.

After loading the bioreactor with medium, the modules 3 are then assembled together to form a stack 4. Several stacks 4 may be operated in tandem. According to the present invention, once assembled, the interior of the bioreactor is isolated from the outside environment. Several stacks 4 may be operated in tandem to give a batch size as large as required. Once the stack 4 is secured, sterilizing fluids, for example steam or gas, are sent into the module, through the communicating channels 11 to sterilize the matrix. Steam is simultaneously sent through the non-communicating channels to heat the bioreactor to a temperature appropriate for sterilization (121° C. for steam, 50° C. for ethylene oxide). In some preferred embodiments, air may be evacuated from the bioreactor by connecting the communicating channels 11 to a vacuum source prior to steaming. The sterilized matrix inside the modules may be cooled by passing cooling water through the non-communicating channels 12 and additionally by passing sterile cool air through the modules 3 of the reactor. During the cooling process, the bioreactor may be held under positive pressure of sterile air until the desired cultivation temperature is reached. Air trapped inside the reactor may be vented if required through the communicating channels. Preferably venting occurs through the vents of alternating plates.

After sterilization, a liquid inoculum of the microorganism to be cultured may be pumped into the modules 3 of the bioreactor stack 4 through the communicating channels 11. The microorganisms cultured in the bioreactor of the present invention may be any bacteria, yeast or fungi. The purpose of culturing these organisms may be for food production or for industrial production of preferred compounds, such as biologically active molecules. Once the appropriate quantity of microorganisms is added to the module and the moisture content is adjusted, the mixer 18 may be turned on for a period of time to mix the inoculum with the solid matrix. The mixer 18 is then stopped and the microorganisms allowed to colonize the matrix. Mixing the inoculum with the matrix prior to fermentation rather than during the fermentation process allow homogeneous distribution of the inoculum before the microorganism has a chance to grow.

During the growth period, the environment inside the bioreactor is monitored, for example by a probe, and carefully maintained. As previously described, sterile air is sent into the bioreactor through the communicating channels 11 to supply the oxygen that is necessary for growth of the microorganisms. The moisture content of the bioreactor can be adjusted by sending liquid into the bioreactor, also through the communicating channels 11. Preferably, the moisture content is adjusted before the step of mixing so that the moisture is equally distributed throughout the matrix. The temperature of the module 3 is controlled by sending water through the non-communicating channels 12. Any of the operations of sterilization, inoculation, temperature control, extraction, and post extraction may be automated with the use of technologies known and used in the art.

The process of fermenting microorganisms generates heat. The buildup of heat inside the bioreactor can be problematic to the fermentation process. One method of removing heat by the present invention is evaporative cooling. Evaporative cooling may be the preferred method of heat removal if it is desirable to remove water from the bioreactor (e.g., if the media contains too much moisture). Evaporative cooling can be achieved by sending air through the 23 plates to the communicating channels and venting the air out the collector plates 24. If it is not desirable to remove water from the bioreactor, it is preferred that the present invention utilizes conduction as the method of heat removal. The method of heat removal by conduction as described herein, requires the passage of cooling fluids through the non-communicating channels 12.

There are two advantages of removing the heat generated during fermentation by conduction. One advantage is that only the amount of air necessary for supplying oxygen needs to be sent into the module 3. The independence from cooling requirements also facilitates the maintenance of any particular atmosphere inside the bioreactor that may be necessary for the cultivation of some particular microorganism. For example, a particular microorganism might require a high carbon dioxide concentration.

A second advantage of removing heat by conduction and not by evaporating moisture from the bed is that conduction does not remove water from the fermentation medium. Evaporative cooling results in water loss from the fermenting medium. If the fermenting medium becomes too dry, this dryness can adversely affect the fermentation growth of the microorganisms. In order to compensate for the lost moisture, the evaporated moisture must be calculated and added back to the fermentation medium.

After moisture replacement, the bed may need to be mixed thoroughly to prevent inhomogeneities in the bed moisture content after the appropriate temperature has been reached. Mixing filamentous microorganisms, such as fungi, results in mycelial breakage and in many cases, especially when carrying out fermentation involving non-septate genera of fungus, for example Rhizhomurcor, results in a drop in the quantity of product produced, therefore it is preferred that mixing occur at the beginning of the fermentation process and be kept to a minimum once fermentation has begun.

Although potentially harmful to certain microorganisms, mixing can prevents excessive moisture pressure drops through the bed due to matted mycelium, especially in the case of fungal fermentations. Even when low air flow is maintained, moisture loss is never eliminated and moisture gradients can develop over a period of several days (e.g., the bioreactor may be dry at the bottom and moist at the top). These gradients are practically eliminated by regularly reversing the direction of the air flow every few hours. The timing of this air flow reversal can be automated so that air flow direction is reversed every few hours (e.g., every four hours). Using this method, homogeneity in moisture content can be maintained throughout the bioreactor.

Heat removal has also been facilitated in part by mixing the fermenting medium during the fermentation process. Besides excessive breakage and damage to the mycelial mass, significant aggregation may also occur, which also results in matting of the mycelium and reduced product quality and yield. Heat removal by conduction avoids the necessity to remove heat by mixing during fermentation.

Microorganisms are often cultivated because they have the ability to produce a bioactive product extracellularly, for example many microorganisms secrete antibiotics. Some microorganisms naturally produce a bioactive product that is of use in biotechnological applications. It is well known in the art that microorganisms can be genetically altered to produce a bioactive product of particular interest. (See Ausubel et all, supra, incorporated herein by reference) Therefore, upon completion of the cultivation period, it may be desirable to extract bioactive molecules from the microorganisms. Extracting fluid, for example an organic solvent, may be sent through the emitter plates 23 into the communicating channels 11 to extract out the metabolites of interest. The extracting fluid is any suitable fluid that can dissolve the product of interest and bring it out of the reactor through the collector plate 24 from so that the product can be recovered. Alternatively, the extraction process may be facilitated by ultra sound or sonication to break the cells. Throughout the duration of the extraction process the temperature of the bioreactor may be controlled to any desired level by passing heating or cooling fluids through the non-communicating channels 12. The ability to use the same device for both fermentation and extraction is a particular advantage provided by the present invention.

In preferred embodiments, the collector plate 24 is attached directly to additional apparatus or apparatus' (e.g., ultrafiltration devices, microfiltration devices or chromatography columns) for purification of the desired product. Attachment is carried out in a manner that maintains a sterile and contained environment. There is not one point in time, from inoculation to collection of the final product, that contamination can occur. Therefore, use of this apparatus eliminates the chance of product contamination by the outside environment if compared with methods previously available. Additionally, a sample of the contents of the bioreactor is an accurate representation of the contents of the bioreactor because the interior environment of the bioreactor is contained and homogeneous. Furthermore, the process of taking a sample to asses whether contamination of the bioreactor has occurred can take place without breaking sterility. A sample that tests negative for contamination guarantees that the entire contents of the bioreactor are sterile. This feature is also advantageous if the product of interest is toxic (e.g., the immunosurpressant cyclosporin). One of ordinary skill in the art will recognize that the extraction process is optional and need not occur in every fermentation process.

Automation of the purification process will allow precise control of all parameters in the entire production procedure. Overall, the bioreactor of the present invention offers an improved method for growing microorganisms and extracting products therefrom, particularly in the aspects of safety and handling of the microorganism. These features make the bioreactor of the present invention an attractive option for growing genetically modified microorganisms grow on a solid substrate. A particular use for of such a bioreactor is growing microorganisms that produce a product that has to meet sterility standards for FDA approval.

After the extraction process is completed, the residual material inside the bioreactor may be treated in any suitable manner while still inside the bioreactor. For example, the material may be treated by heating (e.g., sterilization), cooling, or by reacting the material with a suitable solution. Any manner of treatment that renders the material suitable for disposal can be utilized in the practice of the present invention prior to dismantling the device. Once the stack is dismantled, the residual materials may be disposed and the bioreactor may be washed and reused in another fermentation.

EXAMPLES

The present invention can be further understood through consideration of the following non-limiting Examples.

Example 1

Use of the Bioreactor to Produce & Extract an Extracellular Metabolite (e.g. a Food Product)

3 kilograms of wheat bran was loaded into the modules of the bioreactor having a total plate area of approximately 2500 sq. cm. The bioreactor was assembled and the air was evacuated from the bioreactor by connecting a vacuum to the communicating channels. Following this, steam was sent simultaneously into the communicating as well as the non communicating channels to heat the bioreactor and its contents to a temperature of 121° C. The bioreactor was held at this temperature for 45 minutes, following which, the steam pressure was released. Simultaneously, sterile air was sent into the communicating channels while cooling water at approximately 25 deg C. was sent into the non-communicating channels. When the bioreactor had cooled down to 37 deg centigrade, it was inoculated with a well grown inoculum of a strain of *Rihzhomucorpusillus*, which produces a variety of protease called a milk-clotting-enzyme (also known as a microbial rennet). This enzyme is used in the cheese making industry. The inoculated bran was incubated for a period of 4 days at a temperature of 37° C., to allow the mold to completely colonize the substrate. During this period the temperature of the bran was maintained by circulating warm or cool water through the non-communicating channels. Simultaneously, sterile air at a flow rate of 7 liters/minute was sent into the bioreactor through the communicating channels of alternate plates, and allowed to exhaust out through the communicating channels of the collection plates. The airflow direction was reversed every few hours to prevent moisture gradients in the bed.

After 4 days, 15 liters of water was sent into the communicating channels of the top most plate and allowed to trickle down the stack of plates through the holes in the communicating channels. The aqueous extract, containing the enzyme, was collected from the bottom of the stack. Following this, air was sent into the topmost plate to blow out the maximal amount of residual extract, trapped in the bed. Steam was then sent into the communicating and the non communicating channels to sterilize the extracted moldy bran. This sterilized spent bran was then discarded. The aqueous extract containing the enzyme as then concentrated by ultrafiltration.

Example 2

Use of the Bioreactor to Produce an Intracellular Metabolite e.g. a Pharmaceutical Product 20 kilos of wheat bran was loaded into a bioreactor of approximately 22,600 sq. cm. plate area. The bioreactor was sterilized as described in example 1.

Following sterilization, the bioreactor was cooled to 30 deg C and inoculated with a well grown inoculum of a strain of *Fusarium solanii* which intracellularly produces an immunosuppressant called cyclosporin. Cyclosporin is used to prevent rejection of transplanted organs. The inoculum was mixed thoroughly with the sterilized bran, using the mixing arms, for a period of 1 hour. The inoculated bran was then incubated for a period of 120 hours. Sterile air at a flow rate of 75 liters per minute was sent into the bioreactor continuously. The temperature of the bioreactor was controlled at 29° C. for the first 24 hours, 32° C. for the next 48 hours and finally 29° C. for the last 48 hours.

Following this, the bioreactor was extracted with 120 liters of methanol in the following manner. First, 60 liters of methanol was introduced through the top plate and allowed to trickle into the bioreactor and come into contract with the cultured bran. This methanol was allowed to remain in the bioreactor for a period of 24 hours, to allow the intracellular cyclosporin to diffuse out from the fungal cells into the methanol. This "first soak" was then drained form the bottom plate and replaced with the next lot of 60 liters, which was again allowed to stay in contact with the bran for a period of 6 hours. The second lot was drained and residual extract was flushed out of the bed with air. By following this procedure, an efficient extraction of cyclosporin could be carried out.

The spent bran in the bioreactor was then washed with water to remove traces of residual methanol. The bioreactor was then opened and the spent bran was discharged for disposal. There was no need to sterilize the bioreactor before opening, since the methanol by its nature, had already killed any live material in the bioreactor. The methanol extract, containing cyclosporin, was evaporated in a rotary vacuum evaporator and then purified using column chromatography.

Example 3

Use of the Bioreactor to Produce a Partly Intracellular and Partly Extracellular Metabolite (e.g. a Pharmaceutical Product)

15 kilos of wheat bran was loaded into the bioreactor of approximately 14,500 sq cm. plate area. The bioreactor was sterilized as described below: The bioreactor was assembled and, steam was sent simultaneously into the communicating as well as the non communicating channels of alternate emitter plates to heat the bioreactor and its contents. Simultaneously air and steam were allowed to vent from the communicating and the non-communicating channels of the collector plates in-between (see FIG. 5). The mixing system was also turned on and the contents of the reactor were continuously broken up to dislodge any air pockets, while the venting was in progress. When the temperature of the bioreactor reached 100° C., the venting of steam was stopped. The mixing was also stopped. The reactor was allowed to heat to a temperature of 121° C. The bioreactor was held at this temperature for 60 minutes, following which, the steam pressure was released. Simultaneously, sterile air was sent into the communicating channels while cooling water at approximately 25° C. was sent into the non-communicating channels.

Following sterilization, the bioreactor was cooled to 30° C. and inoculated with a well grown inoculum of a strain of *Aspergillus flavipes* which produces mevinolinic acid. Some of the mevinolinic acid that is produced is secreted into the medium while some of it remains trapped in the fungal mycelium. Mevinolinic acid is used to produce the compound, Lovastatin, which is used in the treatment of hypercholesteremia. The inoculum was mixed thoroughly with the sterilized bran, using the mixing arms, for a period of 1 hour. The inoculated bran was then incubated for a period of 120 hours. Sterile air at a flow rate of 50 lit per minute was sent into the bioreactor continuously. The temperature of the bioreactor was controlled at 30° C. throughout the incubation period. The direction of air flow was changed every hour using automatic control valves.

Following growth, the mixing arms were turned on again for 20 minutes to break up the moldy bran and prepare it for extraction. The bioreactor was extracted with 90 liters of acetone in the following manner. First, 45 liters of methanol was introduced through the top plate and allowed to trickle into the bioreactor and contact the cultured bran. This acetone was allowed to remain in the bioreactor for a period of 16 hours. This "first soak" was then drained from the bottom plate and replaced with the next lot of 45 liters, which was again allowed to stay in contact with the bran for a period of 6 hours. The second lot was drained and residual extract was flushed out of the bed with air.

By following this procedure, an efficient extraction of mevinolinic acid could be carried out. The spent bran in the bioreactor was washed with water to remove traces of residual acetone. The bioreactor was then opened and the spent bran was discharged for disposal. There was no need to sterilize the bioreactor before opening, since the acetone by its nature, had already killed any live material in the bioreactor. The acetone extract, containing mevinolinic acid was evaporated and re-extracted with ethyl acetate. The ethyl acetate extract was evaporated under vacuum to lactonize the mevinolinic acid to lovastatin.

The lovastatin was crystallized out of the ethyl acetate concentrate and purified by re-crystallization in methanol and acetone.

Example 4

Use of the Bioreactor to Produce a Bacterial Enzyme, Useful in the Brewing Industry 1.5 kg of malto-dextrin and 15 kg of Wheat Bran were loaded into a bioreactor of approximately 14,500 square cm area. The contents of the bioreactor were sterilized as explained Example 3. After cooling the reactor, 10 liters of an inoculum of a selected strain *Bacillus subtilis* was transferred to the bioreactor and mixed thoroughly using the mixing arms. This strain of Bacillus produces a mixture of bacterial neutral proteases, betaglucanases and amylases that are useful for producing higher yields of extract from malted barley, in the brewing industry.

The temperature of cultivation was maintained at 32° C. The cultivation time was 72 hours. Following the fermentation, the bioreactor was chilled to 15° C. by circulating chilled water at 10° C., through the non-communicating channels. 60 liters chilled water was then sent into the bioreactor at a flow rate of 15 liters per hour to extract the enzyme completely in 4 hours. Extraction under cold conditions helped to minimize denaturation of this temperature sensitive protease. Following extraction, the reactor was sterilized with steam and the extract was processed using microfiltration and ultrafiltration to yield the final product.

Example 5

Use of the Bioreactor to Produce a Savory Flavoring Agent Using Soy Beans

The bioreactor described in the Examples 3 and 4 was loaded with 10 kg of soy beans and sterilized. It was then inoculated, after cooling, with a strain of *Aspergillus oryzae* and allowed to grow at 30° C. for 2 days. Following the fermentation, the bioreactor was filled with water containing 5% sodium chloride (salt) and the temperature was raised to 50° C. by sending hot water through the non-communicating channels. The mixing arms were turned on periodically for 20 minutes every 6 hours. This condition was maintained for 1 week, during which most of the protein in the soya beans was hydrolyzed. The contents of the reactor were sterilized and the liquid was drained. This liquid was filtered and spray dried to yield a savory flavored protein hydrolysate.

Example 6

Use of Ethylene Oxide to Sterilize the Bioreactor 15 kgs of raw wheat bran of approximately 10% initial moisture, was loaded into a bioreactor of approximately 14,500 square cm area. After the reactor was fully assembled. It was connected to a vacuum source and a vacuum of approximately 28 inches of Hg was allowed to develop. Simultaneously, hot water was circulated in the jacket to bring the temperature of the bioreactor to 50° C. A mixture of ethylene oxide and carbon dioxide in the ration of 90:10 was then sent into the bioreactor. The quantity of the gas was calculated to give a concentration of approximately 760 ppm of ethylene oxide. The ethylene oxide was allowed to remain in the bioreactor for a period of roughly 6 hours, following which a vacuum was again drawn to a level of approximately 28 inches. The vacuum was then broken by sending in carbon dioxide via 0.45 micron sterile filters. The carbon dioxide was then flushed out by sterile air.

The reactor was cooled to 30° C. and inoculated with a well grown inoculum of *Rhizhopus delemar* species, which produces a raw starch hydrolyzing enzyme. It was seen from previous observations that the raw starch hydrolyzing enzyme is more efficiently produced on sterile raw bran, sterilized by ethylene oxide treatment (where the starch has not been gelatinized,) versus bran sterilized by steam at 121° C. (wherein the starch of the bran becomes gelatinized). Raw starch hydrolyzing activity is useful for a variety of applications in the food industry including the production of alcohol.

The culture was allowed to grow for 96 hours at 30° C. Following this incubation, the culture was extracted with water and the extract was concentrated using microfiltration followed by ultrafiltration. The reactor was then sterilized with steam prior to disposal of the contents.

We claim:

1. A bioreactor for cultivating microorganisms on solid medium in such a manner that the bioreactor carries out all steps for cultivating microorganisms in a contained environment, wherein the bioreactor comprises:
   a plurality of modules, the modules capable of being fitted on top of one another to form a stack of modules, wherein each module comprises:
      a base plate containing communicating and non-communicating channels; and
      a frame mounted to the base plate of the module; and
   a mixing arrangement placed within each module.

2. A bioreactor according to claim 1, wherein the bioreactor further comprises a means for sealing the microorganisms within the bioreactor to prevent exposure of the microorganisms to an external environment during operation of the bioreactor.

3. A bioreactor according to claim 1, wherein the bioreactor further comprises a means for controlling the environment of each module.

4. A bioreactor according to claim 1, wherein the bioreactor is made of stainless steel or polycarbonate.

5. A bioreactor according to claim 1, wherein the modules are fitted in such a manner to prevent leakage from within the modules to the outside environment.

6. A bioreactor according to claim 1, wherein the modules are fitted in such a manner to prevent outside contaminants from getting inside the module.

7. A bioreactor according to claim 1, wherein the modules are fitted together by sealing with rubber gaskets.

8. A bioreactor according to claim 1, wherein the dimensions of the module and the size of the stack can be adjusted.

9. A bioreactor according to claim 1, wherein a multiplicity of stacks of modules are operated in parallel.

10. A bioreactor according to claim 1, wherein the modules are a multiplicity of shapes.

11. A bioreactor according to claim 1, wherein the modules are square in shape.

12. A bioreactor according to claim 8, wherein the communicating and non-communicating channels alternate with one another.

13. A bioreactor according to claim 1, wherein the modules are circular in shape.

14. A bioreactor according to claim 7, wherein the communicating and non-communicating channels are arranged radially.

15. A bioreactor according to claim 7, wherein communicating channels are branched for equal distribution of fluids to the module.

16. A bioreactor according to claim 1, wherein the communicating channels are tubes having holes drilled therein for allowing fluids to enter the interior of the module.

17. A bioreactor according to claim 1, wherein the non-communicating channels are tubes for carrying fluids.

18. A bioreactor according to claim 1, wherein the non-communicating channels are formed by spaces between the tubes that form the communicating channels for carrying fluids.

19. The bioreactor of claim 17 or 18, wherein the non-communicating channels carry heating and cooling fluids as a means for controlling the temperature of the modules by conduction.

20. A bioreactor according to claim 1, wherein the communicating channels carry a fluid.

21. A bioreactor according to claim 1, wherein the non-communicating channels carry a fluid capable of conducting heat.

22. A bioreactor according to claim 1, wherein the base plate comprises two metal sheets that sandwich the communicating and non-communicating channels.

23. A bioreactor according to claim 1, wherein the base plate does not have two metal sheets that sandwich the communicating and non-communicating channels.

24. The bioreactor of claim 22, wherein the two metal sheets have a multiplicity of holes drilled therein.

25. The bioreactor of claim 24, wherein the holes correspond to the holes drilled into the communicating channels such that fluids from the communicating channels can enter the interior of the module.

26. A bioreactor according to claim 1, wherein the frame mounted on the base plate forms a container for the solid medium in such manner that the solid medium is in contact with the base plate.

27. A bioreactor according to claim 1, wherein heat is removed from the bioreactor by conduction during cultivation.

28. A bioreactor according to claim 1, wherein the frame height is adjustable.

29. A bioreactor according to claim 1, wherein the frame height is 4–8 cm.

30. A bioreactor according to claim 1, wherein the mixing arrangement is placed at the center of the module for mixing the solid medium.

31. A bioreactor according to claim 1, wherein the mixing arrangement comprises at least two mixing arms.

32. A bioreactor according to claim 1, wherein the mixing arrangement comprises one mixing arm.

33. A bioreactor according to claim 32, wherein the mixing arms are equipped with blades.

34. A bioreactor according to claim 32, wherein the mixing arms are able to rotate.

35. A bioreactor according to claim 32, wherein the mixing arms are able to revolve about the central axis of the module.

36. A bioreactor according to claims 34 and 35, wherein the rotating and revolving are achieved by a two independent shafts.

37. A bioreactor according to claims 34 and 35, wherein the ratio of the speed of revolution to the speed of revolving is fixed to allow equal redistribution of the contents of the bioreactor.

38. A bioreactor according to claim 36, wherein the two independent shafts are driven by at least one independent motor.

39. A bioreactor according to claim 36, wherein the two independent shafts are driven by two independent motors.

40. A bioreactor according to claim 1, wherein the bioreactor further comprises a central distribution port.

41. A bioreactor according to claim 40, wherein the central distribution port is connected to the communicating channels as a means for delivering fluids to the communicating channels.

42. A bioreactor according to claim 40, wherein the central distribution port is a ring.

43. A bioreactor according to claim 1, wherein the bioreactor further comprises a header arrangement.

44. A bioreactor according to claim 43, wherein the header arrangement is connected to the non-communicating channels for bringing fluid into the non-communicating channels.

45. A bioreactor according to claim 1, wherein the bioreactor further comprises a collection port.

46. A bioreactor according to claim 45, wherein the collection port is connected to the non-communicating channels for collecting fluids leaving the non-communicating channels within the base plate.

47. A bioreactor according to claim 45, wherein the collection port is a ring which is concentric with the distribution ring and just inside of the central distribution port.

48. A bioreactor according to claim 47, wherein the diameter of the inner collection ring is larger than the diameter of the distribution ring, thereby allowing fluids coming into the non-communicating channels from the circular header at the periphery to slip over the distribution ring and flow into the collection port and out of the module through the collection ring.

49. A bioreactor according to claim 1, wherein the bioreactor further comprises alternating emitter and collector plates attached to each module of the bioreactor.

50. A bioreactor according to claim 49, wherein fluids enter the module through the emitter plates.

51. A bioreactor according to claim 49, wherein fluids leave the module through the collector plates.

52. A bioreactor according to claim 49, wherein the top emitter or collector plate has holes only in the bottom of the communicating channel and the bottom emitter or collector plate has holes only in the top of the communicating channel.

53. A bioreactor according to claim 49, wherein the emitter plates and collector plates have valves that can be closed such that fluids can be retained in the bioreactor.

54. A bioreactor according to claim 49, wherein the emitter plates and collector plates have valves that can be closed such that pressure inside the bioreactor increases.

55. A bioreactor according to claim 1, further comprising dished ends placed over the top plate and under the bottom plate.

56. A bioreactor according to claim 1, wherein the bioreactor further comprises auxiliary equipment for the operation of the bioreactor.

57. A bioreactor according to claim 1, wherein the bioreactor further comprises an apparatus for purifying an extracted product.

58. A system for solid state fermentation in a bioreactor for cultivating microorganisms in a contained environment, wherein the system comprises:

1) a bioreactor comprising:
   A) a plurality of modules, the modules capable of being fitted on top of one another to form a stack of modules, wherein each module comprises:
      a base plate containing communicating and non-communicating channels; and
      a frame mounted to the base plate of the module; and
   B) a mixing arrangement placed within each module; and
2) a solid state medium disposed in each module.

59. A system for solid state fermentation according to claim 58, wherein the solid state medium is selected from the group consisting of: maize bran, corn, wheat, soya hull, soya beans, cereal, vermiculite, diatomaceous earth, and polyurethane foam.

60. A system for solid state fermentation according to claim 58, wherein the solid state medium is any support material capable of absorbing aqueous solutions.

61. A system for solid state fermentation according to claim 60, wherein the aqueous solution is a nutritive medium.

62. A system for solid state fermentation according to claim 58, and further comprising microorganisms disposed in each module.

63. A system for solid state fermentation according to claim 62, wherein the microorganisms are genetically modified.

64. A system for solid state fermentation according to claim 62, wherein the microorganisms are selected from the group consisting of bacteria, yeast and fungi.

65. A system for solid state fermentation according to claim 64, wherein the fungi is aseptate.

66. A system for solid state fermentation according to claim 64, wherein the fungi is septate.

67. A system for solid state fermentation according to claim 64, wherein the fungi is intracellular septate.

68. A system for solid state fermentation according to claim 64, wherein the fungi is extracellular septate.

69. A system for solid state fermentation according to claim 62, and further comprising a fluid disposed within the communicating channel, wherein the fluid is selected from the group consisting of: steam, air, water, inoculum and organic solvent.

70. A system for solid state fermentation according to claim 62, and further comprising a fluid disposed within the non-communicating channel, wherein the fluid is steam, air, or water.

* * * * *